(12) United States Patent
Zhao

(10) Patent No.: US 7,102,746 B2
(45) Date of Patent: Sep. 5, 2006

(54) RAMAN SPECTROSCOPE

(75) Inventor: Jun Zhao, Albuquerque, NM (US)

(73) Assignee: New Chromex, Inc., Albuquerque, NM (US)

( * ) Notice: Subject to any disclaimer, the term of this patent is extended or adjusted under 35 U.S.C. 154(b) by 93 days.

(21) Appl. No.: 10/737,459

(22) Filed: Dec. 16, 2003

(65) Prior Publication Data

US 2005/0128476 A1   Jun. 16, 2005

(51) Int. Cl.
    *G01J 3/44* (2006.01)
    *G01N 21/65* (2006.01)
(52) U.S. Cl. .................................... 356/301
(58) Field of Classification Search ............... 356/301
    See application file for complete search history.

(56) References Cited

U.S. PATENT DOCUMENTS

| | | | |
|---|---|---|---|
| 5,112,127 A | 5/1992 | Carrabba et al. | 356/301 |
| 5,194,912 A * | 3/1993 | Batchelder et al. | 356/301 |
| 5,377,004 A | 12/1994 | Owen et al. | 356/301 |
| 5,510,894 A | 4/1996 | Batchelder et al. | 356/301 |
| 5,689,333 A * | 11/1997 | Batchelder et al. | 356/301 |
| 5,917,971 A | 6/1999 | Slater | 385/31 |
| 5,943,128 A | 8/1999 | Slater | 356/301 |
| 5,956,136 A * | 9/1999 | Da Silva et al. | 356/301 |
| 6,002,476 A | 12/1999 | Treado | 356/301 |
| 6,028,667 A * | 2/2000 | Smith et al. | 356/301 |
| 6,038,363 A * | 3/2000 | Slater et al. | 385/147 |
| 6,141,095 A | 10/2000 | Allen et al. | 356/301 |
| 6,281,971 B1 | 8/2001 | Allen et al. | 356/301 |
| 6,337,472 B1 * | 1/2002 | Garner et al. | 250/201.3 |
| 6,353,476 B1 | 3/2002 | Allen et al. | 356/301 |
| 6,483,581 B1 | 11/2002 | Ben-Amotz et al. | 356/301 |
| 6,693,280 B1 * | 2/2004 | Sting et al. | 250/339.07 |
| 6,717,668 B1 * | 4/2004 | Treado et al. | 356/327 |
| 6,870,612 B1 * | 3/2005 | Jiang | 356/301 |
| 2003/0025080 A1 | 2/2003 | Sting et al. | 250/339.07 |
| 2004/0263842 A1 * | 12/2004 | Puppels | 356/301 |
| 2005/0185178 A1 * | 8/2005 | Gardner et al. | 356/301 |

FOREIGN PATENT DOCUMENTS

GB  2241350 A  *  8/1991

OTHER PUBLICATIONS

Voor et al., Micro-Raman spectroscopy in the undergraduate research laboratory, Am. J. Phys., vol. 62, No. 5, May 1994, pp. 429-434.*

(Continued)

*Primary Examiner*—F. L. Evans
(74) *Attorney, Agent, or Firm*—Kudirka & Jobse, LLP

(57) ABSTRACT

A compact spectroscope is sufficiently lightweight for use in combination with a microscope for analyzing samples using Raman analytical techniques. The Raman spectroscope includes a housing detachably mountable to the microscope. The housing contains at least one source of radiation. One or more filters are positioned at desired angles across the beam path provided by the source of radiation. The spectroscope includes a variety of components operatively connected to source of radiation capable of providing one or more Raman beams, as well as a variety of components for processing beam constituents for microscope analysis. A fiber optic probe is provided for examining large samples or samples at remote sites. A computer or other electronic reader may also be attached to the Raman spectroscope for viewing analytical data.

43 Claims, 10 Drawing Sheets

OTHER PUBLICATIONS

Zhao et al. Multichannel Fourier Transform Raman Spectroscopy: Combining the Advantages of CCDs with Inteferometry. Nov. 9, 1996 Ohio State University.

Zhao et al. Automated Fluorescence Rejection Using Shifted Excitation Raman Difference Spectroscopy Feb. 25, 2002 Society for Applied Spectroscopy.

Berg et al. Performance of Fiber-Optic Raman Probes for Analysis of Gas Mixtures in Enclosures Aug. 29, 2001 Society for Applied Spectroscopy.

Pelletier Analytical Applications of Raman Spectroscopy 1999 Ann Arbor Michigan.

* cited by examiner

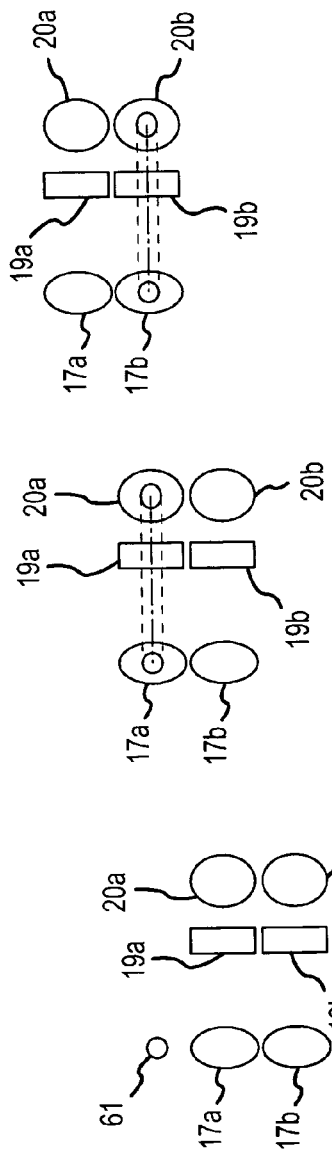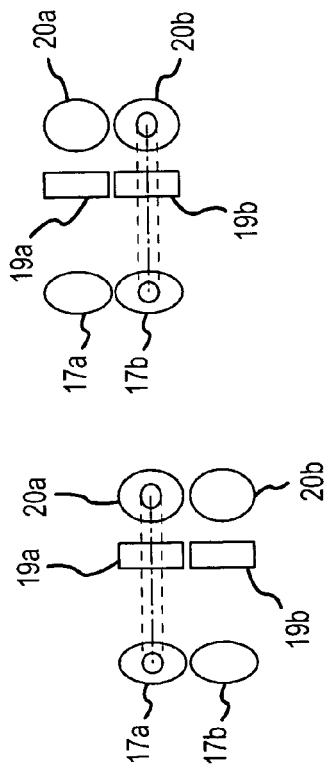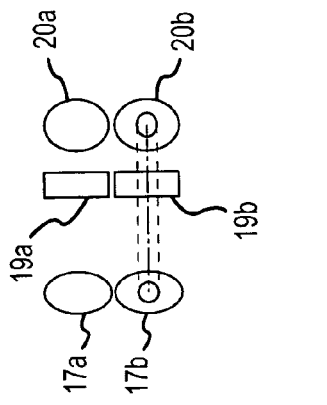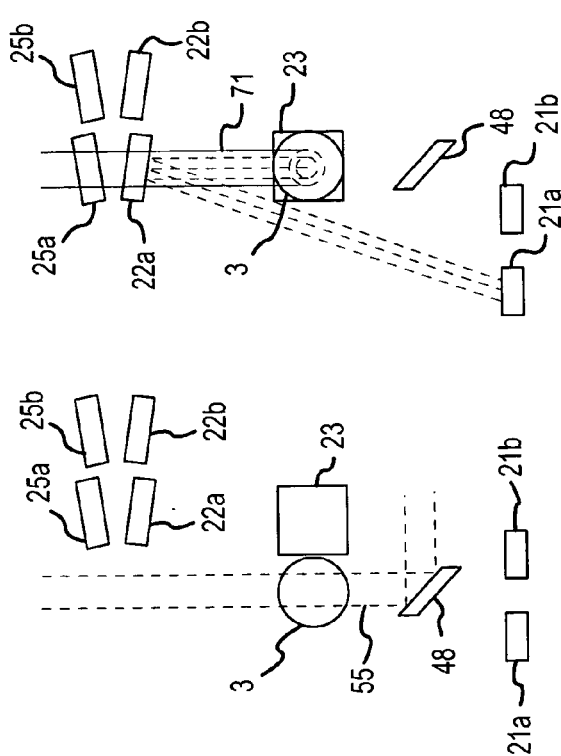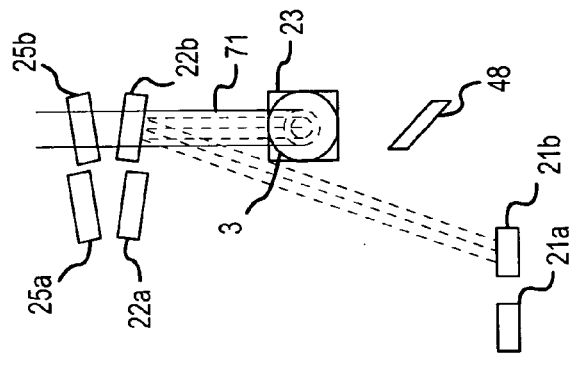

RAMAN SPECTROSCOPE

FIELD OF TECHNOLOGY

The apparatus and method disclosed in this document pertain generally to spectroscopy. More particularly, the new and useful Raman spectroscope claimed in this document is a spectroscopic attachment for a microscope that may include, for example, an infinity corrected light microscope. The Raman spectroscope is particularly, but not exclusively, useful for analysis of samples using Raman spectral analyses techniques.

BACKGROUND

Raman spectroscopy is an analytical technique providing molecule-specific information about a sample. When monochromatic light or radiation strikes material (generally in this document, "incident radiation"), the material (collectively, "sample") will interact with the light. The sample may absorb part of the radiation energy and be raised to an excited electronic state; the sample also may lose part of the absorbed energy through non-radiative relaxation, and may revert to a lower electronic state while releasing reduced energy radiation in the form of fluorescence. A portion of the incident radiation also may be scattered by the sample. Scattered radiation may contain both an elastic component, in which radiation frequencies remain unchanged, and inelastic components with altered frequencies. Elastically scattered components are called Rayleigh scattering; inelastic components, if it is caused by light interacting with the vibrations of molecular bonds, is called Raman scattering.

The frequencies of Raman scattered emissions differ from the incident radiation by the amount of a single, multiple, or combinations of the same or different vibrational frequencies. The amount of the frequency differences is called the "Raman shift," a characteristic of a molecule. The Raman shift, therefore, is useful in analyzing qualitative and quantitative characteristics of a sample. Raman spectra typically contain multiple narrow peaks specific to the chemical identity of a sample, and accordingly can be used in many applications requiring molecular specificity.

Several types of Raman spectroscopic systems have been developed, as well as methods for applying Raman techniques to sample analysis. Exemplary apparatus and methods for using Raman analyses techniques are disclosed in U.S. Pat. No. 6,141,095 issued Oct. 31, 2000 to Allen, et al., U.S. Pat. No. 6,281,971 B1 issued Aug. 28, 2001 to Allen, et al., and U.S. Pat. No. 6,353,476 B1 issued Mar. 5, 2002 to Allen, et al., which references are incorporated into this document.

Typically, a Raman device for spectral analysis contains at least four basic modules: an excitation source, optics for beam steering and signal collection, a spectral analyzer, and a detector. Modern instruments typically use lasers for excitation to provide a wide selection of wavelengths ranging from ultra-violet to near-IR. A spectral analyzer generally decomposes a Raman signal into many constituent frequencies for analysis. A dispersive analyzer, for example, uses a wavelength-dispersing element, such as a grating or prism, to separate different wavelengths. An FT-Raman analyzer may use an interferometer to generate an interferogram from a signal, and transform the signal into the frequency domain through a mathematical procedure. A relatively new form of analyzer uses a tunable filter to pass one frequency at a time, such as an acousto-optic tunable filter, or a liquid crystal tunable filter. Detectors commonly used for Raman spectroscopy include single detectors such as photo multiplier tubes for monochromators working in the visible region, InGaAs or cooled Ge detectors for Fourier Transform ("FT") Raman using near-infrared excitations, multi-channel sensors such as charge coupled devices for spectrographs and imaging spectral analyzers working in the visible and ultraviolet region, and thermal focal plane array detectors in the near-infrared region.

Optics for Raman include laser band pass filters for purifying the monochromatic source, laser rejection filters for removing Rayleigh scattered components before sending a signal to a spectral analyzer, and optics for focusing an excitation beam onto the sample and collecting scattered light from the sample. In the most common configuration, which is called the back-scattering or epi-configuration, the same optics performs both focusing and collecting functions. For examination of remote samples, both the excitation and the signal may be carried through optical fibers over long distances.

Raman microscopy gained popularity during the last decade because of its capability to analyze microscopic samples down to the size of the sub-µm level. In a Raman microscope, the excitation beam is guided into and the signal beam from an objective lens that serves as focusing and collecting optics.

Until now, existing Raman microscopes using dispersive or FT analyzers are designed for use of a microscope that was an attachment to the spectrometer because existing research grade spectral analyzers are typically heavy and bulky. The current invention reverses that trend, and provides a compact Raman spectrometer that may be assembled as an attachment that may be mounted onto a variety of commercially available infinity corrected light microscopes. Instead of treating the microscope as an observation tool for the spectrometer, the Raman spectrometer disclosed and claimed in this document is an accessory or attachment for a microscope, allowing a user to perform spectral analysis on a sample through a microscope. The Raman spectrometer disclosed in this document is designed to accommodate the perspective, desires, and needs of microscopy practitioners, instead of Raman spectrocopists.

Many existing Raman systems are heavy and bulky because they are not designed specifically for microscopy. Their Optical components often have large apertures for high sensitivity, translating into large and heavy components and systems. A compact, and light-weight attachment is achieved by recognizing the unique feature of microscopes: their objective lenses have small apertures. A large optical aperture is not required to capture the signal from an objectives lens. Therefore, smaller optics may be used to achieve reduction in size, weight, and cost. Further reductions in the size, weight and cost due to the laser is possible by the method and apparatus disclosed in U.S. Pat. No. 6,141,095 issued to Allen et al., providing for use of standard diode lasers without frequency stabilization by measuring laser frequencies simultaneously with the Raman. Diode lasers are smaller and less expensive than other lasers.

Another aspect of the Raman spectroscope disclosed and claimed in this document is a means for introducing the laser beam into, and rejecting Rayleigh scattered radiation from, a Raman beam path using edge filters. Edge filters now known in the art typically are interference filters, not holographic notch filters. As will be appreciated by those skilled in the art, to use a back scattering configuration the excitation beam should be introduced into a Raman signal beam path prior to the focusing and collection optics. Thus, the excitation beam and the Raman signal beam should be combined into a common or the same path. Some have suggested such beam combining be achieved using beam splitters, aperture sharing optics, or dichroic filters at 45 degree incident angles. However, conventional beam splitters are inefficient, and aperture sharing is only suitable for collection optics with large apertures. When aperture size approaches that of the laser beam, however, the through-put of aperture sharing becomes very low. Some have suggested overcoming this problem by using a dichroic filter. However, at high incident angles, a dichroic filter is sensitive to the polarization state of light beams, and makes difficult the observation of Raman bands close to the laser line.

Beam-combining optics will reject Rayleigh components to some extent, but the major part of laser rejection may be achieved using interference edge filters and holographic notch filters at near normal incidence, located in the Raman spectrometer between a beam-combiner and the spectral analyzer. Interference filters used for laser rejection may be categorized into two types, edge filters having a wide spectral rejection range, and rugate notch filters having a narrow spectral rejection range. Both types are made of multi-layer thin film coatings of varying refractive indexes deposited on a transparent substrate. Edge filters are used more often than rugate filters because rugate filters are more expensive. Holographic filters, however, made by holographic means, typically have narrow rejection bandwidth, hence the name "notch" filters. The hologram media typically is fragile and requires special protection. In a number of commercially available holographic filters, a thin hologram media layer is sandwiched between two pieces of glass, and the edge is sealed with a special epoxy.

Compared with earlier interference edge filters, holographic notch filters had at least the advantage of a narrower rejection band, thus allowing observation of both Stokes and anti-Stokes Raman. Their edges also are steeper, allowing observation of Raman bands close to a laser line, down to less than 100 cm$^{-1}$ Raman shift. The Raman transmission curve also is smoother and flatter, inducing less severe ripples to the observed spectrum. High quality interference filters, however, can match or exceed the performance of state-of-the-art holographic notch filters on the Stokes side of the Raman spectrum.

A second aspect of the Raman spectrometer disclosed and claimed in this document is the use of interference filters at low incident angles as beam combiners. The use of holographic filters at both large (45 degree) and small (less than 45 degree) incidence angles as beam-combiners to inject a laser beam into an optical path and to reject Rayleigh scattering has been suggested. The low (much less than 45 degree) incidence angle arrangement avoided the polarization effect of 45 degree dichroic mirror and allowed the observation of Raman lines very close to the laser frequency. However, it is known that holographic filters may induce fluorescence from the incident laser; they also are subject to damage from environmental factors such as moisture leaking into the hologram media. Performance of holographic filters made with current technology typically degrades over time. Interference edge filters and rugate filters, typically made of multi-layer hard oxide coatings, however, may be used for long periods of time without degradation. Also, because holographic filters are made individually, they cost much more than interference edge filters. If an interference edge filter or a rugate filter is used in a Raman spectrometer as a beam combiner, at low incidence angles less than 45 degrees, typically between 10 and 0 degrees, significant performance and low-cost advantages are achieved over holographic filters.

SUMMARY

The Raman spectroscope, which is compact and sufficiently lightweight to be mountable on microscope, is combinable with a microscope for analyzing a sample. The spectroscope includes a housing that is detachably mountable to the microscope. The housing contains at least one source of radiation. The spectroscope includes a variety of components operatively connected to source of radiation capable of providing one or more Raman beams from the source of radiation. In addition, the Raman spectroscope includes within the housing a variety of components for processing beam constituents for microscope analysis. A fiber optic probe may be attached to the housing for examining large samples or samples at remote sites. A computer or other electronic reader may also be attached to the Raman spectroscope for showing analytical data.

Another aspect of the current invention provides means for introducing the laser beam into and rejecting Rayleigh scattered radiation out of the Raman beam path using interference filters, not holographic filters. The filter is oriented such that both the laser beam and the Raman beam are incident at an equal angle, which is substantially less than 45 degrees and typically between 10 and 0 degrees. Using high performance interference filters offers significant advantage over holographic filters on both lifetime and cost.

It will become apparent to one skilled in the art that the claimed subject matter as a whole, including the structure of the apparatus, and the cooperation of the elements of the apparatus, combine to result in a number of unexpected advantages and utilities. The advantages and objects of the Raman spectroscope will become apparent to those skilled in the art when read in conjunction with the accompanying following description, drawing figures, and appended claims.

The foregoing has outlined broadly the more important features of the invention to better understand the detailed description that follows, and to better understand the contributions to the art. The Raman spectroscope is not limited in application to the details of construction, and to the arrangements of the components, provided in the following description or drawing figures, but is capable of other embodiments, and of being practiced and carried out in various ways. The phraseology and terminology employed in this disclosure are for purpose of description, and therefore should not be regarded as limiting. As those skilled in the art will appreciate, the conception on which this disclosure is based readily may be used as a basis for designing other structures, methods, and systems. The claims, therefore, include equivalent constructions. Further, the abstract associated with this disclosure is intended neither to define the Raman spectroscope, which is measured by the claims, nor intended to limit the scope of the claims. The novel features of the Raman spectroscope are best understood from the accompanying drawing, considered in connection with the accompanying description of the drawing, in which similar reference characters refer to similar parts, and in which:

BRIEF DESCRIPTION OF THE DRAWING

FIGS. 6A–6C are top schematic views of alternative multiple sets of mirrors and laser band pass filters;

FIGS. 7A–7C are top schematic views of alternative multiple sets of mirrors, and laser rejection filters;

DETAILED DESCRIPTION

As described in greater detail below, the Raman spectrometer disclosed in this document is a compact spectroscope sufficiently lightweight for use in combination with a microscope for analyzing samples using Raman alnalytical techniques. The Raman spectroscope includes a housing detachably mountable to the microscope. The housing contains at least one source of radiation that generates incident radiation. One or more filters are positioned at desired angles across the beam path provided by the source of radiation. The spectroscope includes a variety of components operatively connected to source of radiation capable of providing one or more Raman beams, as well as a variety of components for processing beam constituents for microscope analysis. A fiber optic probe is provided for examining large samples or samples at remote sites. A computer or other electronic reader may also be attached to Raman spectroscope for viewing analytical data.

Figure 1:
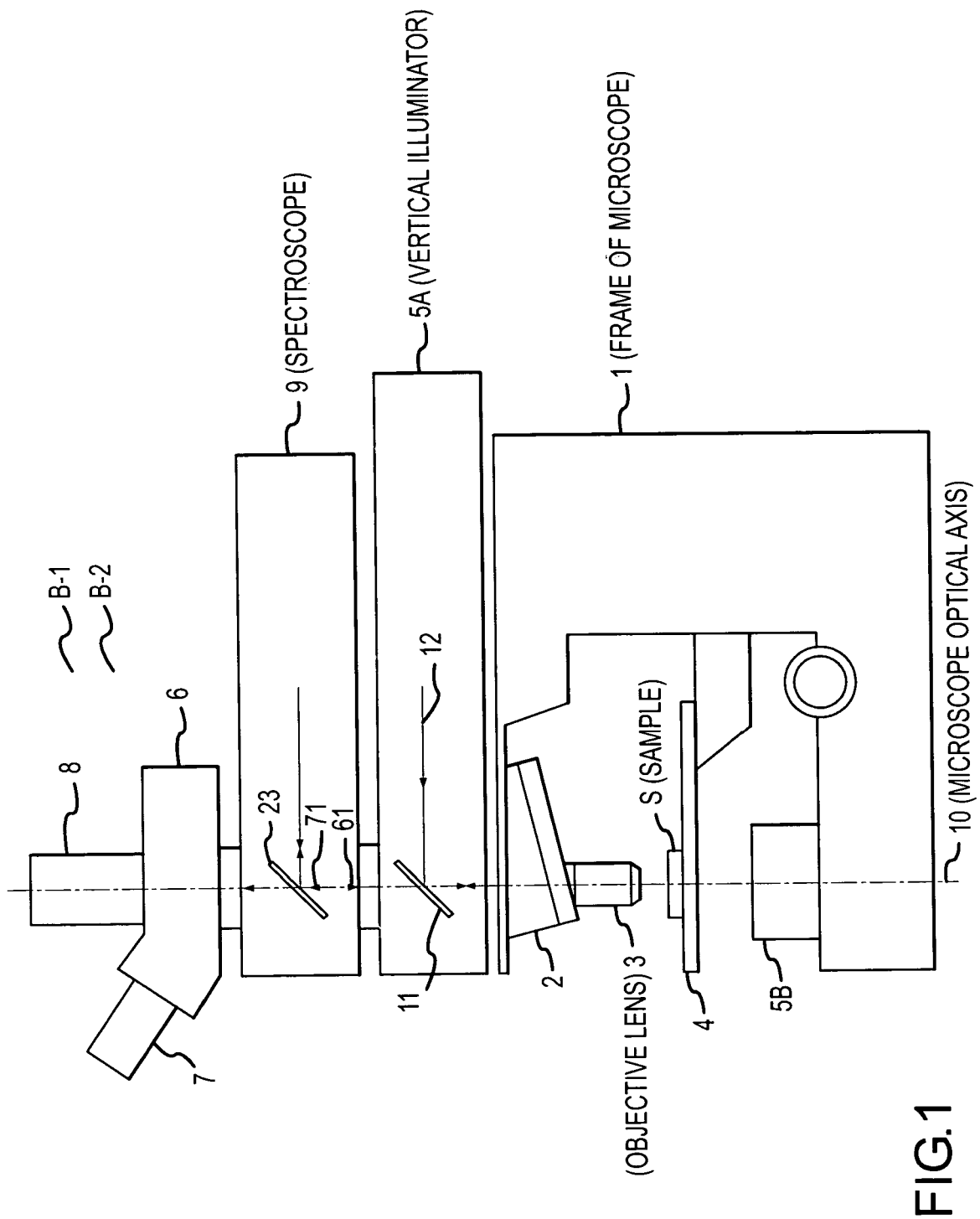
FIG. 1 is a side schematic view of the Raman spectroscope mounted on a microscope.

More specifically, as shown in FIG. 1, Raman spectroscope 9 is detachably mountable on a microscope B-1. Microscope B-1 is an infinity corrected light microscope B-2. Infinity corrected light microscope B-2 typically consists of at least the following components: a frame 1, a multiple objective turret 2, at least one objective lens 3, a sample stage 4, at least one illuminator 5 and a viewing device 6. Illuminator 5 may include a reflected light illuminator 5A, the latter commonly called a vertical illuminator, or epi-illuminator. Illuminator 5 alternatively or also may include a transmitted light illuminator/condenser 5B. Viewing device 6 may support one or more eyepieces 7. Viewing device 6 may also support a camera 8, and is called either a binocular or trinocular (used interchangeably in this document).

In infinity corrected microscope B-2, visible light gathered from a sample, shown diagrammatically as "S" in FIG. 1, is collimated by objective lens 3, and is formed into an image by a tube lens (not shown), usually located within viewing device 6. Because light is collimated between objective lens 3 and the tube lens, many components may be inserted in this region without substantially affecting imaging quality. For example, microscope B-2 can be used with or without epi-illuminator. It is within this region that Raman spectroscope 9 is located. When an epi-illuminator is present, although its location and that of Raman spectroscope 9 are interchangeable, Raman spectroscope 9 may be placed between an epi-illuminator 5A and a binocular or trinocular 6 to preserve the Kohler illumination of epi-illuminator 5A. Raman spectroscope 9 has mechanical means formed between epi-illuminator 5A and trinocular 6, where first mode mirror 23 is movably mounted as shown by cross-reference to FIG. 2, which optically couples objective lens 3 to Raman spectroscope 9 when positioned in optical axis 10, as also shown by cross-reference to FIG. 2. Trinocular 6 is used for normal viewing when mode mirror 23 is moved from optical axis 10. For maximum Raman sensitivity, mode mirror 23 reflects the majority of excitation and Raman energy, but also transmits a small fraction of laser light to view the laser spot on sample S using viewing device 6. When laser and Raman wavelengths lie outside the visible light spectrum, mode mirror 23 can be made dichroic, which provides high reflectance for the excitation and Raman light as well as high transmittance for visible light. Mode mirror 23 may remain in optical axis 10 continuously for both Raman analysis and normal sample viewing using either eyepiece 7 or video camera 8. If, however, there is significant overlap between the visible and the Raman spectrum, such as when visible laser wavelengths are used for excitation, normal microscope viewing capability may be sacrificed when mode mirror 23 is in optical axis 10.

When epi-illuminator 5A is placed between Raman spectroscope 9 and objective turret 2, an objective is to cause laser beam 61 and Raman beam 71 as shown in FIG. 1 to pass through epi-illuminator 5A un-attenuated to maximize Raman signal collection efficiency. Epi-illuminator 5A has at least one optical element 11 located in optical axis 10, as shown in FIG. 1, that directs at least a portion of illumination light 12 onto sample S through objective lens 3, and passes at least a portion of the light collected by objective lens 3 into viewing device 6. For bright field illumination, at least one element 11 may be a beam splitter (not shown), while for dark field observation, at least one element 11 may be a ring mirror (not shown) with a hollow center. Thus, when performing Raman analysis on sample S the bright field beam splitter may be moved from optical axis 10, while a dark field ring mirror may remain in optical axis 10 to, allow laser beam 61 and Raman beam 71 to pass through the hollow center un-attenuated.

Figure 2:
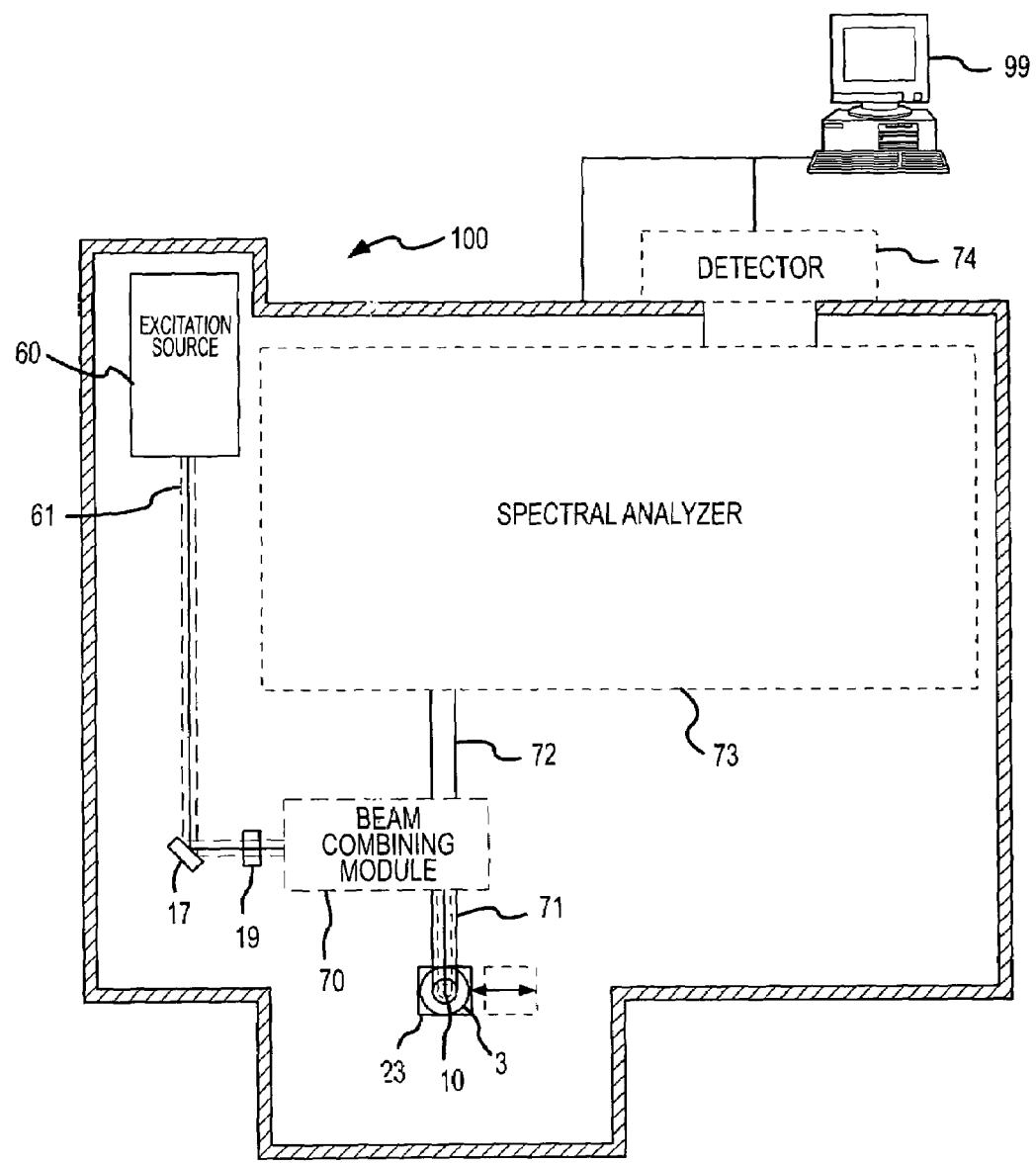
FIG. 2 is a top schematic view of the Raman spectroscope.

FIG. 2 is a schematic of the top view of some customary components of Raman spectroscope 9, also identified by reference numeral 100.

A mirror 17 directs the excitation beam 61 from the excitation source 60 to a band pass filter 19. Band pass filter 19 removes emissions other than the desired wavelength. Excitation beam 61 is redirected by a beam-combining module 70, and reflected by mode mirror 23 toward objective lens 3 to be focused by objective lens 3 onto sample S. Scattered light beam 71 is collected by the same objective lens 3, reflected by first mode mirror 23, through beam combining module 70, after which any Rayleigh scattered light is partially rejected to produce a purified Raman beam. Purified Raman beam 72 is passed through spectral analyzer 73 to detector 74. Mode mirror 23 may be moved into optical axis 10 for Raman analysis, and moved away from optical axis 10 for normal viewing with microscope B-1.

Figure 3A:
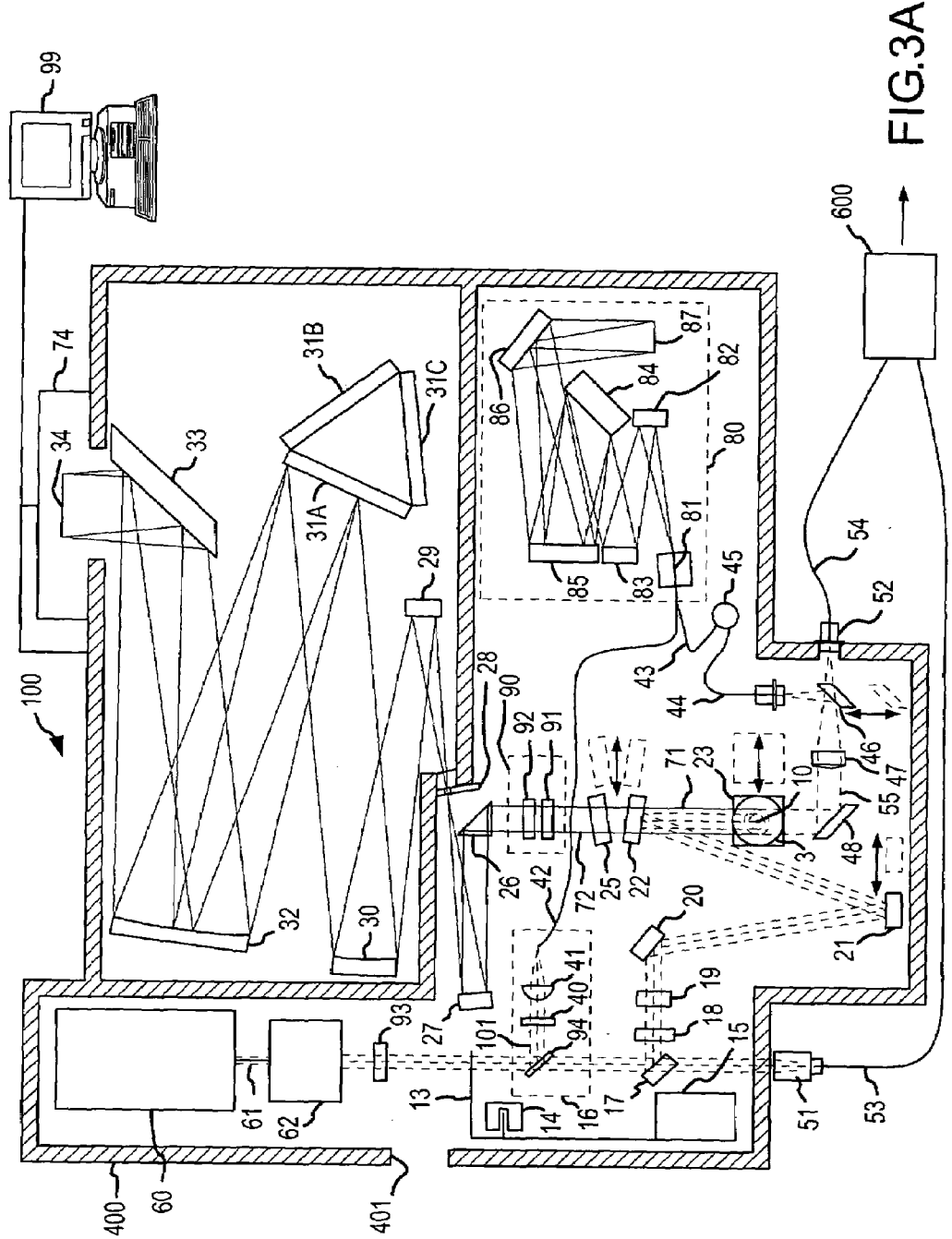
FIG. 3A is another top schematic view of the Raman spectroscope showing a variety of components.

As shown in FIG. 3A, Raman spectroscope 100 may include other components. Excitation beam 61 from a computer controlled excitation source 60 is shown passing through a beam expander 62 and an optional polarization rotator 93 to be discussed below. Beam expander 62 modifies beam size and collimation so that a diffraction limited laser spot size is obtained on an objective focal plane. When a refractive objective lens 3 is used on microscope B-1, chromatic aberration may require different degrees of collimation or divergence for different excitation wavelengths to obtain a diffraction limited laser spot size on the focal plane of objective lens 3. This can be achieved by adjusting beam expander 62 until the smallest spot size is obtained on a flat sample surface that is in visual focus of infinity corrected microscope B-2. A shutter blade 13 mounted onto an actuator 15 controlled by the computer 99 normally blocks beam 61. Shutter blade 13 is operatively connected to a sensor 14 to sense the open/closed state of shutter blade 13. Shutter blade 13 opens only when receiving an "open" command from computer 99. If shutter blade 13 opens accidentally, computer 99 will command excitation source 60 to shut down to avoid possible human injury or damage to sample S. When shutter blade 13 is opened, excitation beam 61 passes through an optional beam-sampling module 16. Beam 61 is reflected by mirror 17 to a power control unit 18, which controls the amount of optical power transmitted by one of several means, such as a variable neutral density filter, multiple discreet neutral density filters, or at least one polarizer (collectively, not shown). All optical elements in power control unit 18 are of sufficient quality that the direction and degree of collimation of excitation beam 61 is not affected when power level is changed. Excitation beam 61 passes band pass filter 19, which purifies beam 61 by reflecting or absorbing all but peak wavelength of excitation beam 61.

Beam combining module 70 shown in FIG. 2, in this embodiment shown in FIG. 3A, includes one or more mirrors 20 and 21, and a low incident angle interference edge filter 22. Interference filter 22 reflects excitation beam 61 from mirror 21, toward mode mirror 23. Interference filter 22 is oriented at a low incident angle, much less than 45 degrees, preferably between 0 and 10 degrees, to avoid any polarization effects. As will be described later, interference filter 22 partially rejects the Rayleigh component from scattered light beam 71 and transmits the Raman component, thus fulfilling the dual role of introducing excitation beam 61 into the path of Raman beam 71, while rejecting Rayleigh scattering from Raman beam 71.

Figure 3B:
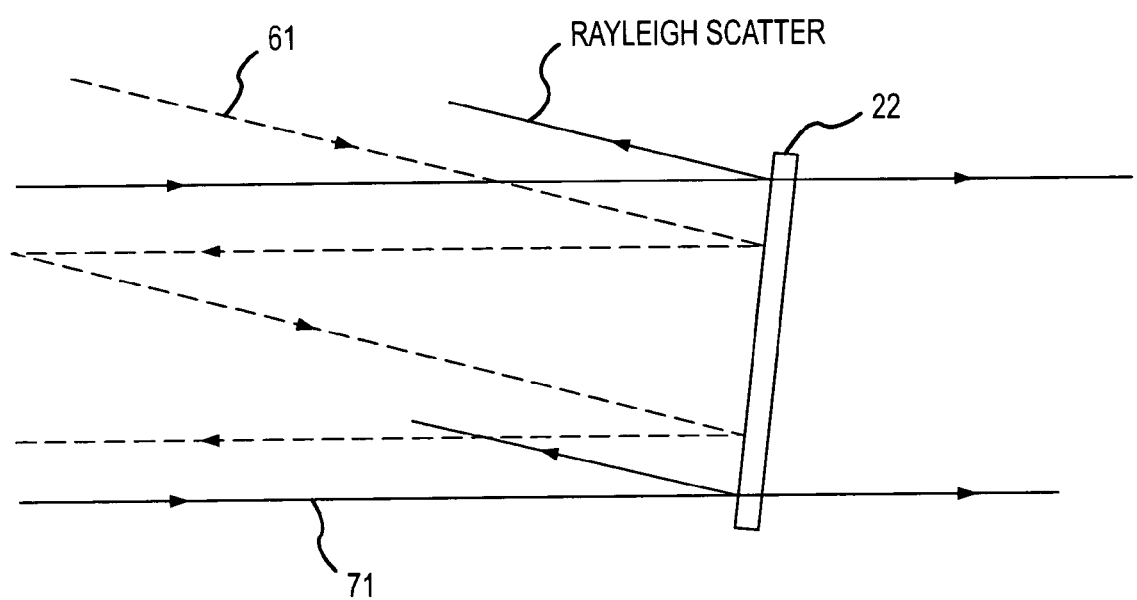
FIG. 3B is a schematic view of an interference filter at a low incident angle to inject by reflection the excitation beam into the Raman beam path, and to reject by reflection Raleigh scattered component from the Raman beam.

Beam combining module 70 may have other forms of embodiment as discussed earlier, including a beam splitter, dichroic mirror, an aperture sharing mirror, or an holographic filter at a low incident angle (collectively, not shown). However, as discussed earlier, the present configuration is more advantageous. Although currently embodied in Raman spectroscope 100, using one or more interference filters 22 at low incident angle to inject laser beam 61 and reject Raleigh scattering from Raman beam 71, as shown in FIG. 3B, may be used in other instruments such as Raman probe 600.

Figure 3C:
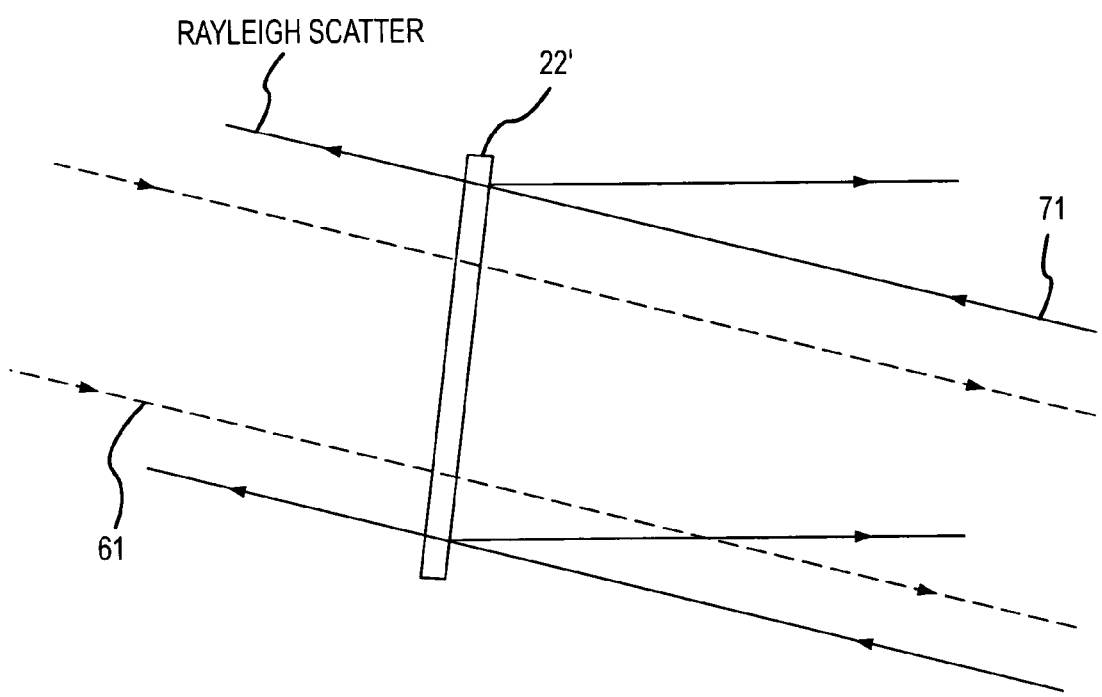
FIG. 3C is a schematic view of using an optical filter at a low incident angle to inject by transmission the excitation beam into the Raman beam path, and to reject by transmission the Raleigh scattered component from the Raman beam.

Another effective way of introducing the laser beam into the Raman beam path using optical filters at low incident angles is shown in FIG. 3C, where the excitation beam is transmitted while the Raman beam is reflected by the filter 22'. This arrangement requires the filter 22' to have different optical properties than the filter 22 shown in FIG. 3B, and it may be either a holographic filter or an interference filter. Specifically, in FIG. 3C, the excitation beam is incident upon the optical filter 22' at a small angle, which is much less than 45 degrees and typically between 0 and 10 degrees. The optical filter 22' transmits a majority portion of the excitation beam intensity. The collected Raman beam traveling in the opposite direction of the excitation beam is incident upon the said optical filter at the same small angle, which is much less than 45 degrees and typically between 0 and 10 degrees. Filter 22' transmits a majority portion of the Rayleigh scattering intensity, while reflects a majority portion of the Raman scattering intensity.

Mode mirror 23 reflects laser beam 61 toward objective lens 3. Objective lens 3 focuses laser beam 61 onto sample S, collects and collimates scattered light from sample S, and projects it upward to mode mirror 23. Scattered light beam 71 is collinear with excitation beam 61 until intercepted by interference filter 22. Interference filter 22 partially reflects the Rayleigh scattered component in an opposite direction from laser beam 61 incident on interference filter 22, and passes the Raman scattered component as a useful signal. One or more additional filters 25 may achieve additional Rayleigh rejection. Purified Raman beam 72 is reflected from a right angle prism 26, as shown in FIG. 3, and focused by a concave mirror 27 onto an entrance aperture 28 of spectral analyzer 73. Using concave mirror 27 as a focusing element produces no chromatic aberration, but has the disadvantages of geometric aberrations due to off-axis use. However, the geometric aberrations may be reduced to insignificant levels by aligning concave mirror 27 at small off-axis angles. Likewise, a lens (not shown) can be used to focus purified Raman beam 72 if chromatic aberration is controlled below an acceptable level.

Although spectral analyzer 73 as shown in FIG. 2 may be provided in varying configurations as discussed earlier, a standard Czerny-Turner spectrograph is suggested in FIG. 3A. Purified Raman beam 72 entering a variable entrance aperture 28, as perhaps best shown in FIG. 4, may be reflected by an alternative mirror 29 onto concave mirror 30. Concave mirror 30 collimates Raman beam 71 and directs it to one or more diffraction gratings 31a–c. The one or more diffraction gratings 31a–c is on a computer controlled precision turret (not shown). More than one grating may be needed to offer both high spectral resolutions and wide spectral ranges, and to accommodate more than one excitation wavelength. Gratings disperse a light beam into collimated beams of different diffractive angles according to their wavelengths, and a second concave mirror 32 focuses the collimated beams onto sensor area 34 of detector 77, preferably a CCD detector. A third mirror 33 may be used to fold the converging beam for optimal mounting of the detector 34. Detector 77 may be thermoelectrically cooled to lower any dark noise.

Figure 4:
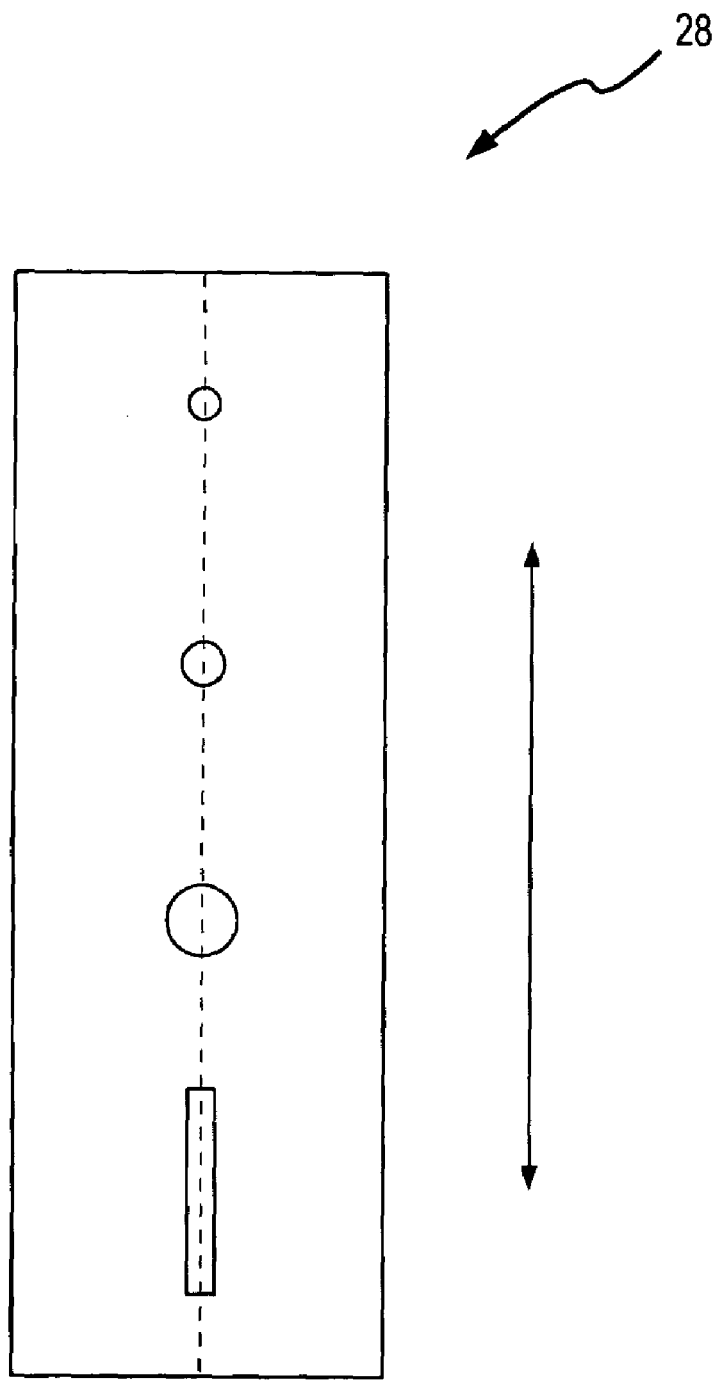
FIG. 4 is a schematic front view of the variable aperture array.

As shown in FIG. 4, entrance aperture 28 may include an array of different sizes of pinholes and slits to allow both conventional and confocal Raman analysis of the sample. Typical pinhole diameters may vary from 20 um to 100 um for confocal Raman microscopy. Hole size is affected by focal length of concave mirror 27, as well as the wavelength of the light. A slit of 50 um wide and 500 um long may be useful for non-confocal Raman, and for acquisition using fiber probe 600. Each pinhole and slit is precisely positioned to where the Raman beam is focused by focusing optics 27. Entrance aperture 28 is mounted on a precision translation stage (not shown), and each aperture is selected preferably by a computer controlled motorized actuator (not shown).

FIG. 3A also shows an optional polarization module 90 that may be inserted in the path of Raman beam 71 to analyze the polarization state of Raman peaks. Polarization module 90 may include a polarization filter 91 and a polarization scrambler 92. Another optional feature may include a quarter wave plate 93 inserted in laser beam path 61 prior to beam combining module 70, which can rotate the polarization of excitation beam 61. Both optional polarization module 93 and optional polarization module 90 are slidable into and out of the optical paths. Raman peaks usually are polarized, and the polarization state is indicative of molecular orientation and the symmetry of the vibrational mode of the sample.

Optional beam sampling module 16 includes beam sampler 94 for reflecting a portion of excitation beam 61 but passes the majority of it. Sampled excitation beam 101 then passes through one or more attenuation filters 40 to be focused into an optical fiber 42 by lens 41. Optical fiber 42 sends excitation light to optional mini-spectrometer 80 to characterize frequencies and intensities.

As shown in FIG. 3A, to analyze sample S when difficult to locate on sample stage 4 of microscope B-1, fiber probe 600 may be used in conjunction with Raman spectroscope 100. For this purpose, as shown in FIG. 3A, fiber coupler 51 is mounted onto a wall facing laser beam 61. Mirror 17 is mounted on a vertical slide (not shown). When mirror 17 is moved from the path of laser beam 61, the laser beam 61 enters fiber coupler 51 that focuses laser beam 61 into optical fiber 53. For better directional reproducibility of laser beam 61, Mirror 20 may be mounted on the same vertical slide to move with mirrors 17. Optical fiber 53 thus may carry laser light to a Raman probe 600 shown in FIG. 3A. A number of fiber optic Raman probes are commercially available to deliver laser energy through one or more fibers 53 onto sample S, to collect a Raman signal, and sending the Raman signal through a second optical fiber 54. Second fiber 54 is coupled to fiber adapter 52, which is mounted on a wall of Raman spectroscope 100. A diverging Raman beam from fiber 54 is collimated by collimating lens 47, and collimated Fiber-borne Raman beam 55 is reflected by reflecting mirror 48 toward spectral analyzer 73. Mode mirror 23 should be moved from the optical path for collimated Fiber-borne Raman beam 55 to pass.

Many commercial fiber optic Raman probes, 600, as shown in FIG. 3A, include efficient Rayleigh rejection filters obviating the need for filters 22 and 25. Accordingly, additional Rayleigh rejection filters would decrease throughput without added benefit. Thus, for maximum sensitivity, low incident angle interference edge filter 22 and additional filter 25 should be moved from the Raman beam 71 path using a movable slide (not shown). For better directional reproducibility of laser beam 61, mirror 21 may be mounted onto the same slide to move together with low incident angle interference edge 22 and additional filter 25. However, if probe 600 does not provide sufficient Rayleigh rejection, low incident angle interference edge filter 22 and additional filter 25 may remain in optical path of Raman beam 71.

The method for calibrating Raman and excitation frequencies disclosed in U.S. Pat. No. 6,141,095 and is incorporated into this document. The means for calibration of the Raman frequency includes neon lamp 45 as shown in FIG. 3A, which emits atomic emission lines of known frequencies, second optical fiber 44 that carries neon emissions, and movable mirror 46, which when moved in the optical path of fiber-borne Raman beam 55 reflects light from second optical fiber 44 toward collimating lens 47. Thereafter, the neon light follows the same path as the fiber-borne Raman beam 55 from fiber 54 used for external Raman probe 600. Neon lamp 45 is turned on and off through computer 99. Movable mirror 46 is moved from the light path of fiber-borne Raman beam 55 when external Raman probe 600 is in use. The means for calibrating laser frequency include neon lamp 45, a lamp connected optical fiber 43, optical fiber 42 carrying sampled laser beam 101, and second spectral analyzer 80. At the entrance aperture of second spectral analyzer 80, lamp-connected optical fiber 43 and optical fiber 42 are merged into single fiber 81. Second spectral analyzer 80 may include many configurations, including an interferometer, or a spectrograph similar to spectral analyzer 73. The mixed sampled laser beam 101 and neon light from single fiber 81 is reflected by a planar mirror 82 and further collimated by second concave mirror 83, dispersed by second grating 84, and focused by third concave mirror 85 onto second CCD detector 87 through fourth mirror 86. A laser spectrum from second CCD detector 87, and the Raman spectrum from detector 74, is acquired simultaneously, and calibrating both into frequencies in $cm^{-1}$ allows direct calculation of the Raman shift.

Figure 5:
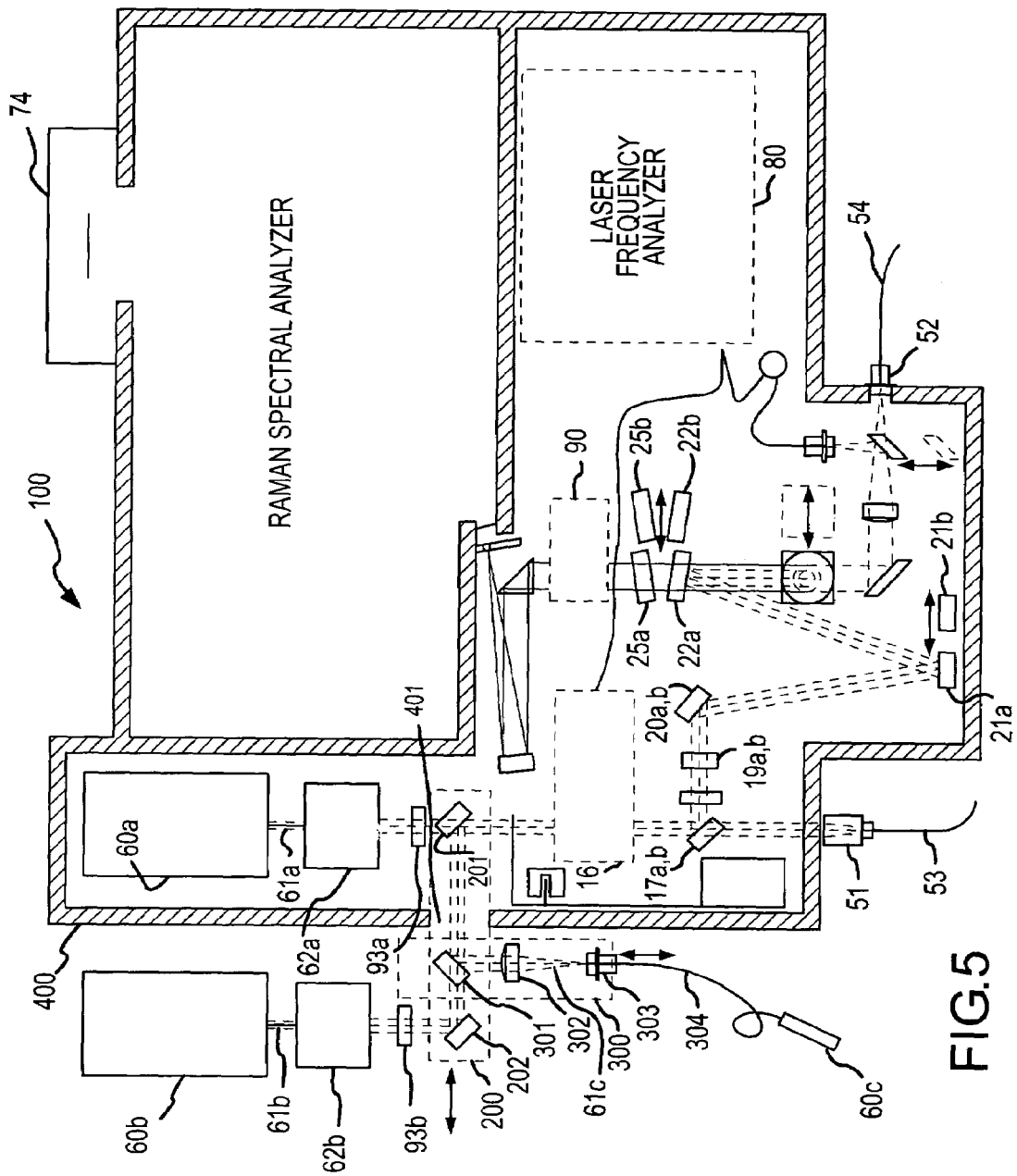
FIG. 5 is a top schematic view of the Raman spectroscope showing alternative embodiments.

FIG. 5 shows an alternative embodiment having a second excitation source 60*b* used to provide greater capability for Raman spectroscope 100. Secondary laser beam 61*b* is introduced through opening 401 in the side plate 400. The excitation source 60, laser beam 61, beam expander 62, and optical polarization rotator 93, as shown in FIG. 3A thus have two corresponding equivalents, which include the excitation sources 60*a,b*, laser beams 61*a,b*, beam expanders 62*a,b*, and optical polarization rotators 93*a,b*, as shown in FIG. 5. Beam changing module 200 includes a pair of beam changing mirrors 201 and 202 mounted on a single slide. When beam changing module 200 is moved into the laser path of secondary excitation source 60*b*, beam 61*b* is directed by mirror 202 and 201 into the same path as 61*a*. Alternatively, the primary excitation source 60*a* is used. Excitation sources 60*a,b* are preferably of different wavelengths. For example, one may be a 785 nm diode laser, and the other a 532 nm solid-state laser. Because both are compact and lightweight, they are suitable for use in Raman spectroscope 100. Alternatively, beam changing mirror 201 can be replaced with a dichroic mirror to reflect wavelength of 60*b* and pass wavelength of 60*a*.

Yet a third excitation source shown as 60*c* may be utilized for Raman spectroscope 100 as shown in FIG. 5. Beam changing module 200 may be used in conjunction with beam changing module 300. Third excitation source 60*c* may be a stand-alone laser too heavy or bulky to be mounted on the attachment and its wavelength may be different from 60*a* and 60*b*. Beam changing module 300 includes an optical fiber adapter 303, a collimating lens 302, and a mirror 301 mounted on a single movable slide (not shown). Power from excitation source 60*c* is delivered to Raman spectroscope 100 using an optical fiber 304 coupled to optical fiber adapter 303. Light from optical fiber 304 is collimated by collimating lens 302, reflected by mirror 301 to second reflecting mirror 201, and into the path of beam 61*a*. Optical fiber 304 is preferably a single mode fiber to obtain the smallest laser spot on sample S when microscope B-2 is used. Alternatively, optical fiber 304 may be a multimode fiber when external fiber probe 600 is used in this case. Mirrors 17*a,b* are moved from the laser path 61 and the beam is focused into optical fiber 53. Mirror 301 may be replaced with dichroic mirror to reflect the wavelength of external laser 60*c*, and pass wavelength of secondary laser 60*b*.

In order to accommodate two different excitation wavelengths for use with the microscope, the wavelength specific elements shown in FIG. 3A, including band pass filter 19, beam combiner 22, and Rayleigh rejection filter 25, now must have two sets of optics, a and b, each for one out of the three possible different wavelengths provided by the three possible sources 60*a,b*, and *c*. Thus, as shown in FIGS. 6A–6C, mirrors 17*a* and 17*b*, filters 19*a* and 19*b*, and mirrors 20*a* and 20*b*, are mounted on a single vertical slide, which has three positions. In FIG. 6A, the slide is in its lowest position, and the laser beam 61, which may carry any one of three possible wavelengths, goes into the fiber coupler 51. In FIG. 6B, the middle position, the excitation wavelength corresponding to filter 19a is coupled to the microscope, and in 6C, the highest position, the excitation wavelength corresponding to filter 19b is coupled to the microscope. Similarly, as shown in FIGS. 7A–7C, mirrors 21a and 21b, filters 22a and 22b, filters 25a and 25b are mounted on a single horizontal slide, which also has three positions. In FIG. 7A, the slide is in its right most position, the mode mirror 23 is moved out, and the Fiber-borne Raman beam 55 from the external fiber probe goes into the spectral analyzer. In this case, fiber probe 600 may use any one of the three possible wavelengths from 60a,b, or c. In FIG. 7B, the middle position, the excitation wavelength corresponding to filters 22a and 25a is coupled to the microscope, and in 7C, the most left position, the excitation wavelength corresponding to filters 22b and 25b is coupled to the microscope.

A method for automatically removing fluorescence background associated with Raman spectroscopy is disclosed in a U.S. Pat. No. 6,281,971, incorporated into this document, assigned to New Chromex, Inc., and described in a publication entitled "Automated Fluorescence Rejection Using Shifted Excitation Raman Difference Spectrosopy", by Jun Zhao et. al, Applied Spectroscopy, 2002, 56(7), 834. At least one of three possible excitation sources 60a,b or c has a wavelength tunable within a narrow range. A single mode 785 nm diode laser can be wavelength tuned by changing diode temperatures. Two Raman spectra are acquired of the same sample at two slightly different excitation wavelengths, and their difference spectrum is processed automatically through an integral transform to yield a fluorescence free Raman spectrum.

Figure 8:
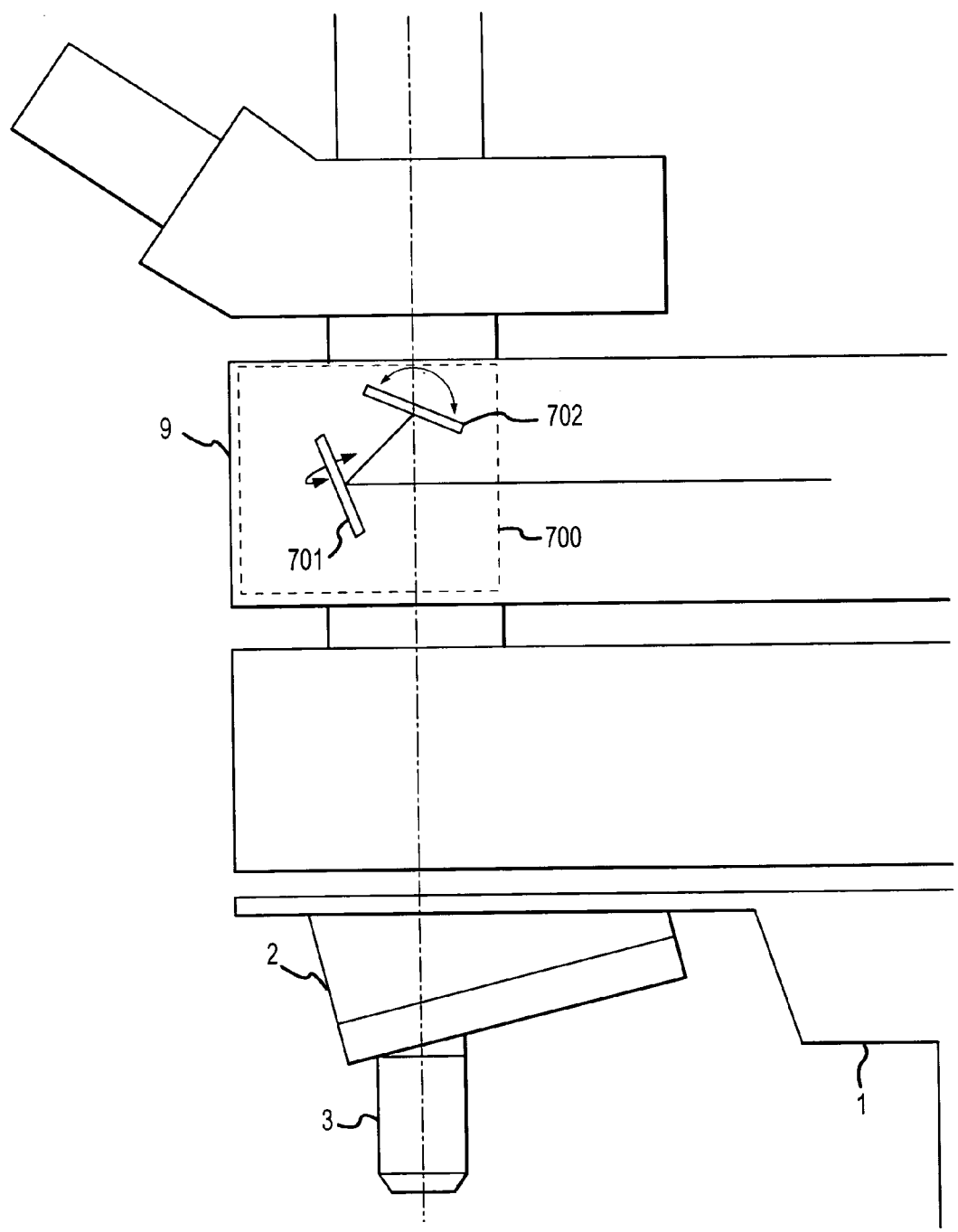
FIG. 8 is a side schematic view of another embodiment of the Raman spectrometer using a pair of scanning mirrors.

The intensity of a Raman band may be mapped over a two dimensional area or a three dimensional volume of sample S by measuring a spectrum on each spot within the sample area or volume, thereby creating a two-dimensional or three dimensional Raman image of sample S. Spectral images are useful for visualizing composition distribution on sample S. Two dimensional spectral mapping can be done by moving either sample S with the X-Y stage of microscope B-2, or the laser spot using a scanning mirror module 700 in place of first mode mirror 23, as shown in FIG. 8. Fast, accurate laser scanning can be achieved by using a pair of galvanometric mirrors 701, 702 with orthogonal scanning axes, arranged as shown in FIG. 8. Depth dimension is added by moving sample S using the Z stage of microscope B-2. Combined with the confocal capability of Raman spectroscope 9, high spatial resolution spectral images can be obtained on a variety of samples, including semiconductor surfaces and biological tissues.

Figure 9:
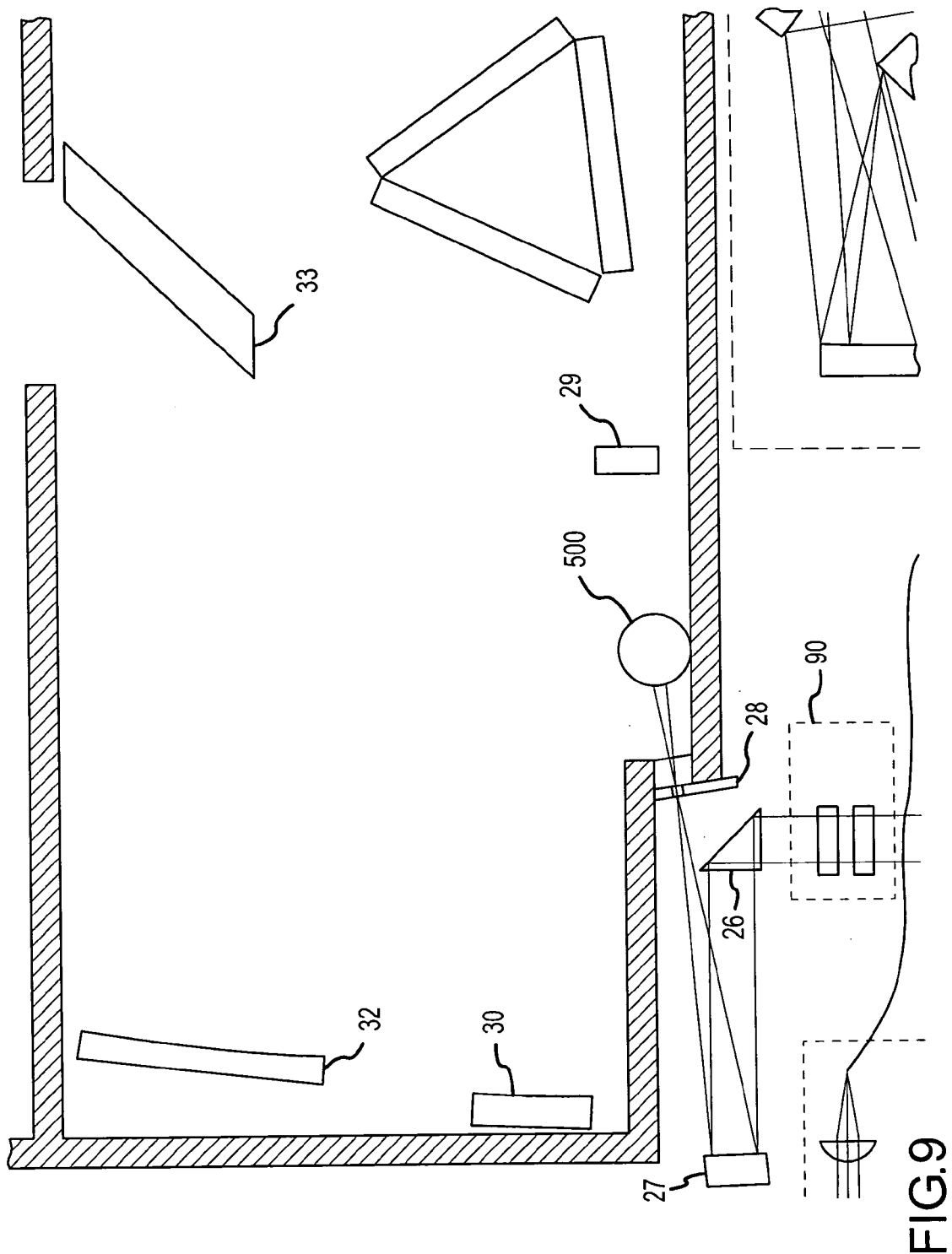
FIG. 9 is a top schematic view of another embodiment of the Raman spectroscope with an optional PMT (photomultiply tube) detector for fluorescence microscopy.

As shown in FIG. 9, a removable fluorescence detector 500, such as a PMT or avalanche photodiode, may be inserted in the optical path of spectral analyzer 73, behind entrance aperture 28, to provide the ability to perform confocal fluorescence microscopy. Confocal fluorescence microscopy is an important technique to study biological samples, including living cells, often stained with fluorescent dyes. The main spectral differences between fluorescence and Raman are intensity and spectral resolution. A fluorescence spectrum is often broad and lacks sharp peaks, thus high spectral resolution is not needed, while a Raman spectrum typically contains multiple sharp and narrow bands, therefore requires high spectral resolution. In term of intensity, fluorescence is often many orders of magnitude stronger than the Raman signal when the excitation wavelength is matched to the fluorescence dye. Therefore confocal fluorescence imaging can be performed with a single detector, which has high readout speed but no spectral resolution, and a PMT is an ideal detector for such a purpose. Combined with fast scanning galvanometric mirrors, high-resolution confocal fluorescence images can be obtained in a matter of seconds or less.

Raman spectroscope 9 as shown in drawing FIGS. 1 through 9 shows a variety of embodiments not intended to be exclusive, but merely illustrative of Raman spectroscope 9.

Claim elements and steps in this document have been numbered and/or lettered solely as an aid in readability and understanding. The numbering is not intended to, and should not be considered as, intending to indicate the ordering or sequencing of elements and steps in the claims.

What is claimed is:

1. A Raman spectroscope attachment, comprising:
a spectral analysis apparatus, wherein the spectral analysis apparatus comprises a Raman spectrometer and is detachably mountable on a microscope.

2. A Raman spectroscope attachment as recited in claim 1, further comprising a source of radiation installed in the spectral analysis apparatus for providing at least one excitation beam.

3. A Raman spectroscope attachment as recited in claim 2, wherein the microscope includes at least one objective lens.

4. A Raman spectroscope attachment as recited in claim 3, further comprising a beam-combining module mountable in the path of the at least one excitation beam installed in the spectral analysis apparatus for directing an excitation beam to the at least one objective lens.

5. A Raman spectroscope attachment as recited in claim 2, further comprising means for focusing the excitation beam on a sample and for collecting Raman data from the sample.

6. A Raman spectroscope attachment as recited in claim 2, wherein the source of radiation is monochromatic.

7. A Raman spectroscope attachment as recited in claim 1, wherein the spectral analysis apparatus includes a spectral analyzer.

8. A Raman spectroscope attachment as recited in claim 1, wherein the spectral analysis apparatus includes a detector.

9. A Raman spectroscope attachment as recited in claim 1, wherein the spectral analysis apparatus includes one or more optical devices.

10. A Raman spectroscope attachment as recited in claim 1, wherein the Raman spectroscope attachment further comprises at least one electronic device for viewing compiled data.

11. A Raman spectroscope attachment as recited in claim 4, wherein the beam-combining module is selected from the group of beam-combining modules consisting of dichroic mirrors, mirrors provided with one or more holes, beam splitters, holographic filters, and interference filters.

12. A Raman spectroscope attachment as recited in claim 11, wherein the beam-combining module includes means for redirecting a scattered Raman beam into the Raman spectral analysis apparatus, and further wherein the beam-combining module directs the excitation beam through the objective lens.

13. A Raman spectroscope attachment as recited in claim 2, wherein the spectral analysis apparatus further comprises at least one Rayleigh rejection filter.

14. A Raman spectroscope attachment as recited in claim 13, wherein the at least one Rayleigh rejection filter is selected from the group of filters consisting of interference filters, edge filters, rugate filters, and holographic filters.

15. A Raman spectroscope attachment as recited in claim 14, wherein the at least one Rayleigh rejection filter is capable of reflecting the at least one excitation beam while passing a Raman scattered beam.

16. A Raman spectroscope attachment as recited in claim 15, wherein the at least one Rayleigh rejection filter is oriented such that the angle of incidence of the at least one excitation beam is substantially less than 45 degrees.

17. A Raman spectroscope, comprising:
 a Raman spectral analysis apparatus that includes a source of radiation, wherein the spectral analysis apparatus is detachably mountable on a microscope; and
 at least one interference filter installable in the Raman spectral analysis apparatus, wherein the at least one interference filter is adjustably positionable within a range of predetermined angles.

18. A Raman spectroscope as recited in claim 17, wherein the source of radiation is monochromatic.

19. A Raman spectroscope as recited in claim 17, wherein the spectral analysis apparatus includes a spectral analyzer.

20. A Raman spectroscope as recited in claim 17, wherein the spectral analysis apparatus includes a detector.

21. A Raman spectroscope as recited in claim 17, wherein the spectral analysis apparatus includes one or more optical devices.

22. A Raman spectroscope as recited in claim 17, wherein the Raman spectroscope further comprises at least one fiber optic probe.

23. A Raman spectroscope as recited in claim 17, wherein the Raman spectroscope further comprises at least one electronic device for viewing analysis data.

24. A Raman spectroscope as recited in claim 17, wherein the interference filter is an edge filter.

25. A Raman spectroscope as recited in claim 17, wherein the at least one interference filter is a rugate filter.

26. A Raman spectroscope as recited in claim 17, wherein the at least one interference filter is adjustable such that an angle of incidence of a beam output by the source of radiation is within a range from 0 degrees to 10 degrees.

27. A spectroscope system, comprising:
 an infinity corrected light microscope for analyzing a sample;
 a housing detachably mountable on the microscope;
 at least one source of radiation positionable in the housing for producing one or more beam paths; and
 means operatively connectable to the at least one source of radiation for analyzing Raman spectra from the one or more beam paths, wherein the Raman spectra analyzing means includes one or more filters.

28. A spectroscope system as recited in claim 27, further comprising a fiber optic probe detachably mountable to the housing for examining samples.

29. A spectroscope system as recited in claim 28, wherein the one or more Raman beams analyzing means includes a spectral analyzer.

30. A spectroscope system as recited in claim 29, wherein the spectral analyzer is selected from the group of spectral analyzers consisting of dispersive analyzers, Fourier Transform analyzers, interferometers, and tunable filters.

31. A spectroscope system as recited in claim 30, wherein the one or more Raman beams analyzing means includes a detector.

32. A spectroscope system as recited in claim 31, wherein the one or more filters is an edge filter.

33. A spectroscope system as recited in claim 31, wherein the one or more filters is a rugate filter.

34. A spectroscope system as recited in claim 33, wherein the one or more filters is positionable in relationship to the beam path at an angle ranging from 0 degrees to 10 degrees.

35. A spectroscope as system as recited in claim 34, further comprising means for detachably mounting the housing to the microscope.

36. A spectroscope system as recited in claim 35, wherein the microscope mounting means are selected from the group of mounting means consisting of reciprocal dovetail connections, slides, slots, locks, clamps, nuts, bolts, and connectors.

37. A method of manufacturing a compact spectrometer for a microscope, comprising:
 providing a source of incident radiation for analyzing constituents of a sample;
 selecting low costs, light weight, small mass components for directing the incident radiation through the compact spectrometer;
 equipping the compact spectrometer with one or more interference filters;
 including in the compact spectrometer a Raman spectral analyzer;
 and providing the spectrometer with a mounting apparatus that allows the spectrometer to be detachably mountable to the microscope;
 positioning in the compact spectrometer a detector; and
 disposing one or more fiber optic probes detachably mountable to the compact spectrometer for analyzing alternative samples.

38. A method of manufacturing a compact spectrometer for a microscope as recited in claim 37, wherein the source of incident radiation providing step includes the substep of providing at least one diode laser to enhance compactness of the compact spectrometer.

39. A method of manufacturing a compact spectrometer for a microscope as recited in claim 37, wherein the source of incident radiation providing step includes the substep of providing a beam path through the compact spectrometer.

40. A method of manufacturing a compact spectrometer for a microscope as recited in claim 37, wherein the one or more interference filters equipping step includes the substeps of selecting the one or more interference filters from the group of interference filters consisting of edge filters and rugate filters.

41. A method of manufacturing a compact spectrometer for a microscope as recited in claim 37, wherein the one or more interference filters equipping step includes the substep of positioning the one or more interference filters at an angle to the beam path ranging from 0 degrees to 10 degrees.

42. A method of manufacturing a compact spectrometer for a microscope as recited in claim 37, wherein the one or more interference filters equipping step includes the substep of positioning the one or more interference filters at an angle to the beam path ranging from 0 degrees to 15 degrees.

43. A method of manufacturing a compact spectrometer for a microscope as recited in claim 37, wherein the spectral analyzer including step includes the substeps of:
 including one or more dispersive analyzers;
 including one or more FT-Raman analyzers;
 including one or more interferometers; or
 including one or more tunable filters.

* * * * *